(12) United States Patent
Glaser et al.

(10) Patent No.: US 11,761,574 B2
(45) Date of Patent: *Sep. 19, 2023

(54) LOCKING RELEASE SYSTEMS FOR ARTICULABLE ELEMENTS AND METHODS OF OPERATING THE SAME

(71) Applicant: GCX Corporation, Petaluma, CA (US)

(72) Inventors: Robert Peter Glaser, Corte Madera, CA (US); Joshua Kawarii Littlefield, Santa Rosa, CA (US); Cristian J. Daugbjerg, Novato, CA (US); Paul Rene Borloz, Petaluma, CA (US)

(73) Assignee: GCX Corporation, Petaluma, CA (US)

( * ) Notice: Subject to any disclaimer, the term of this patent is extended or adjusted under 35 U.S.C. 154(b) by 118 days.

This patent is subject to a terminal disclaimer.

(21) Appl. No.: 17/359,014

(22) Filed: Jun. 25, 2021

(65) Prior Publication Data

US 2021/0317944 A1 Oct. 14, 2021

Related U.S. Application Data

(63) Continuation of application No. 16/261,468, filed on Jan. 29, 2019, now Pat. No. 11,047,522, which is a
(Continued)

(51) Int. Cl.
*F16M 11/20* (2006.01)
*F16M 11/24* (2006.01)
(Continued)

(52) U.S. Cl.
CPC ......... *F16M 11/2092* (2013.01); *A47B 21/03* (2013.01); *A47B 21/0314* (2013.01);
(Continued)

(58) Field of Classification Search
CPC .. F16M 11/2092; F16M 11/12; F16M 11/048; F16M 11/2014; F16M 11/24; F16M 13/02; F16M 13/022; A61B 2090/506
See application file for complete search history.

(56) References Cited

U.S. PATENT DOCUMENTS 5,108,063 A 4/1992 Koerber et al.
5,257,767 A 11/1993 Mcconnell
(Continued)

FOREIGN PATENT DOCUMENTS

EP 1156261 A2 11/2001

*Primary Examiner* — Eret C McNichols
(74) *Attorney, Agent, or Firm* — Perkins Coie LLP

(57) ABSTRACT

Various embodiments concern locking release mechanisms that allow an articulated support arm to be moved between various vertical orientations. A locking release mechanism may include a handle release mechanism positioned within the handle of the articulated support arm, and a gas spring release mechanism positioned within the body of the articulated support arm. The articulated support arm can include a gas spring that remains locked until the handle release mechanism is activated, e.g. by applying pressure to a grip actuator. Other embodiments concern cable management techniques for articulated support arms. Oftentimes, an articulated support arm will include cables routed through the arm that are configured to support an attachment. For example, the cable(s) may be adapted for audio signals, video signals, power, etc. The cable(s) can be readily cleaned and/or serviced when routed through an articulated support arm composed of one or more removable pieces.

19 Claims, 16 Drawing Sheets

Related U.S. Application Data continuation of application No. 15/142,954, filed on Apr. 29, 2016, now Pat. No. 10,203,064.

(51) Int. Cl.

| | |
|---|---|
| *F16M 13/02* | (2006.01) |
| *F16G 11/12* | (2006.01) |
| *A61G 12/00* | (2006.01) |
| *F16M 11/04* | (2006.01) |
| *A47B 21/03* | (2006.01) |
| *A61G 13/10* | (2006.01) |
| *F16M 11/10* | (2006.01) |
| *A61B 90/50* | (2016.01) |

(52) U.S. Cl.
CPC ......... *A61G 12/004* (2013.01); *A61G 12/005* (2013.01); *A61G 13/107* (2013.01); *F16G 11/12* (2013.01); *F16M 11/046* (2013.01); *F16M 11/048* (2013.01); *F16M 11/10* (2013.01); *F16M 11/2014* (2013.01); *F16M 11/2021* (2013.01); *F16M 11/2064* (2013.01); *F16M 11/24* (2013.01); *F16M 13/02* (2013.01); *F16M 13/022* (2013.01); *A47B 2021/0321* (2013.01); *A61B 2090/506* (2016.02); *F16M 2200/021* (2013.01); *F16M 2200/041* (2013.01); *F16M 2200/048* (2013.01); *F16M 2200/06* (2013.01); *F16M 2200/063* (2013.01); *F16M 2200/065* (2013.01)

(56) References Cited

U.S. PATENT DOCUMENTS

| | | | |
|---|---|---|---|
| 5,791,263 A * | 8/1998 | Watt | A47B 21/0314 |
| | | | 108/138 |
| 5,992,810 A | 11/1999 | Crinion et al. | |
| 6,038,986 A | 3/2000 | Ransil et al. | |
| 6,076,785 A | 6/2000 | Oddsen, Jr. | |
| 6,336,618 B1 | 1/2002 | Barber | |
| 6,471,165 B2 | 10/2002 | Twisselmann | |
| 6,783,105 B2 | 8/2004 | Oddsen, Jr. | |
| 6,971,624 B2 | 12/2005 | Kollar et al. | |
| 7,013,813 B2 | 3/2006 | Lima et al. | |
| 7,140,306 B2 | 11/2006 | Chen | |
| 7,597,298 B2 | 10/2009 | Papendieck et al. | |
| 7,597,299 B2 * | 10/2009 | Papendieck | F16M 11/24 |
| | | | 248/281.11 |
| 8,359,982 B2 | 1/2013 | Lebel et al. | |
| 9,228,696 B2 * | 1/2016 | Borloz | F16M 11/046 |
| 9,888,766 B2 | 2/2018 | Chuang | |
| 10,695,250 B2 | 6/2020 | Tao et al. | |
| 2003/0178541 A1 | 9/2003 | Barber | |
| 2004/0188578 A1 | 9/2004 | Turner | |
| 2007/0095993 A1 | 5/2007 | Yamamoto | |
| 2008/0111039 A1 | 5/2008 | Wiegandt et al. | |
| 2008/0149794 A1 | 6/2008 | Yamamoto et al. | |
| 2012/0235000 A1 | 9/2012 | Daugbjerg et al. | |
| 2014/0339377 A1 | 11/2014 | Tao et al. | |
| 2016/0084432 A1 | 3/2016 | Chuang | |
| 2016/0091117 A1 | 3/2016 | Boccoleri et al. | |
| 2016/0109056 A1 | 4/2016 | Chen et al. | |
| 2017/0020280 A1 | 1/2017 | Chuang | |
| 2018/0140089 A1 | 5/2018 | Blackburn | |

* cited by examiner

LOCKING RELEASE SYSTEMS FOR ARTICULABLE ELEMENTS AND METHODS OF OPERATING THE SAME

CROSS-REFERENCE TO RELATED APPLICATIONS

This application is continuation of U.S. patent application Ser. No. 16/261,468, filed on Jan. 29, 2019, which is a continuation of U.S. patent application Ser. No. 15/142,954, filed on Apr. 29, 2016, and issued as U.S. Pat. No. 10,203,064 on Feb. 12, 2019, both of which are incorporated by reference herein in its entirety.

RELATED FIELD

Various embodiments relate generally to mechanical arms. More specifically, various embodiments relate to locking mechanisms for variable height mechanical arm structures and cable management techniques.

BACKGROUND

Mechanical arms are often used to support a wide variety of objects, such as display monitors and work surfaces. These mechanical arms typically provide stationary, adjustable, and/or movable support. For example, the mechanical arms may be moved laterally, rotated, tilted, etc.

Mechanical arms can also be used in a wide variety of environments, including biologically-sensitive environments such as hospitals, laboratories, medical and/or dental offices, and hospices. However, conventional mechanical arms generally include structures, e.g. covers, fasteners, trim, pivots, that are readily contaminated by dirt, dust, grease, germs, blood, sweat, chemicals, etc. As such, these structures are not readily and thoroughly cleanable when exposed.

Although some conventional mechanical arms are able to provide adjustable height, these arms are not designed for frequent adjustment and heavy use. Screen movement is often sloppy and/or uncontrolled, which causes the joints to loosen quickly. Thus, conventional arms generally do not offer high performance over a full range of positions. Further yet, many conventional designs also include pinch points and exposed gaps, which are not readily cleanable.

SUMMARY

Locking release mechanisms for variable-height articulated support arms are described herein that allow the articulated support arms to be readily moved between various vertical orientations upon being released. More specifically, the locking release mechanism includes a handle release mechanism positioned within the handle of the articulated support arm, and a gas spring release mechanism positioned within the body of the articulated support arm. The articulated support arm can include a gas spring that remains locked, i.e. the piston will not move freely, until the handle release mechanism is activated. The locking release mechanism translates a force applied to the handle release mechanism, such as the squeezing motion of a user's hand, into a force that depresses the tip of the gas spring, which causes the gas spring to unlock and the articulated support arm to be freely moveable. Upon removal of the force from the handle release mechanism, the gas spring tip returns to lock the gas spring (and the articulated support arm) into a particular position.

Management techniques for cables routed through an articulated support arm are also described here. Oftentimes, an articulated support arm will include one or more cables internally routed through the arm that are configured to support one or more attachments. For example, the cable(s) may be adapted for audio signals, video signals, power, etc. Various embodiments described herein include a protective outer shell that includes one or more removable pieces, which allow a user to easily access components within the articulated support arm. Together with any non-removable pieces, the removable piece(s) preferably form a smooth surface that is entirely or substantially free of gaps, ridges, tight corners, or heavy textures that would make cleaning difficult.

BRIEF DESCRIPTION OF THE DRAWINGS

One or more embodiments of the present invention are illustrated by way of example and not limitation in the figures of the accompanying drawings, in which like references indicate similar elements.

DETAILED DESCRIPTION

Figure 1:
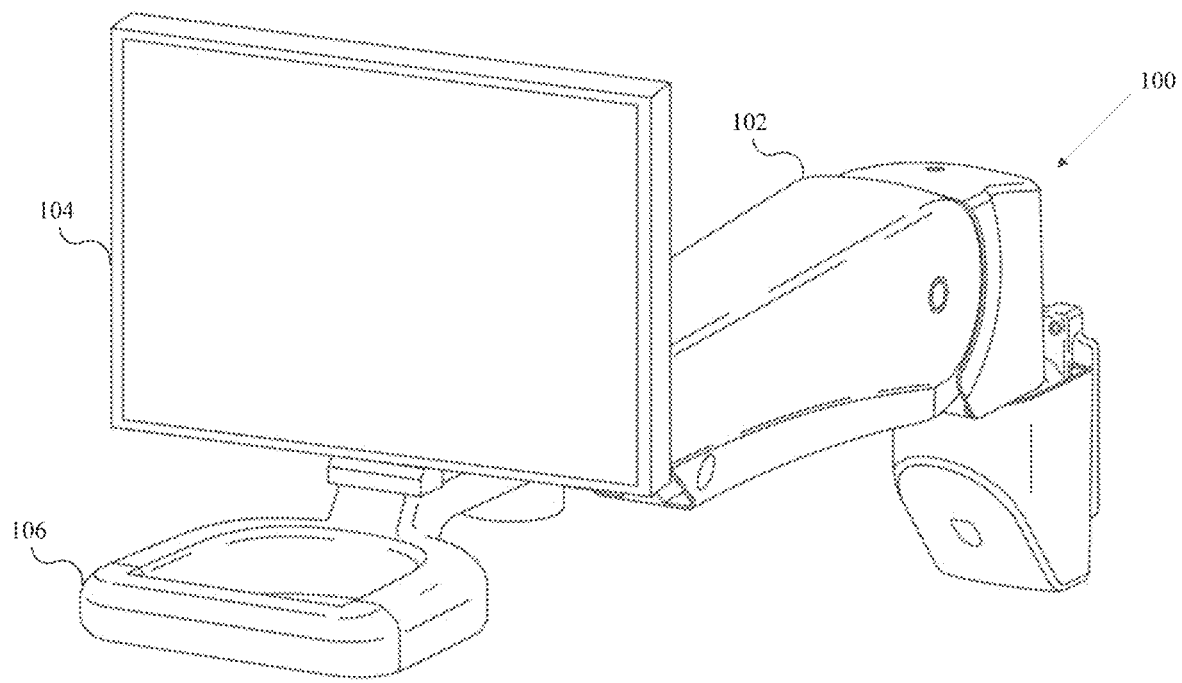
FIG. 1 is a perspective view of an articulated support arm supporting a monitor.

Locking release mechanisms are described herein that allow articulated support arms to be readily moved between various vertical orientations upon being released. More specifically, the locking release mechanism includes a handle release mechanism positioned within the handle of the articulated support arm, and a gas spring release mechanism positioned within the body of the articulated support arm. The articulated support arm can include a gas spring that remains locked, i.e. the piston will not move freely, until the handle release mechanism is activated, e.g. by applying pressure to a grip actuator. The lockable gas spring provides the necessary counter-balance support force for the rest of the articulated support arm assembly.

The locking release mechanism translates a force applied to the handle release mechanism, such as the squeezing motion of a user's hand, into a force that depresses the tip of the gas spring, which causes the gas spring to unlock and the articulated support arm to be freely moveable. More generally, when a force is applied to a grip actuator in the handle, e.g. a squeeze plate, the locking release mechanism causes the gas spring to be remotely released, which enables vertical arm motion. Upon removal of the force from the handle release mechanism, the gas spring tip returns to lock the gas spring (and articulated support arm) into a particular position. For example, the return action could be caused by a combination of the internal gas spring pressure and one or more coil springs. The handle release mechanism and gas spring release mechanism can be coupled together with a Bowden-style control cable assembly.

Conventional release mechanisms are fixed directly onto the end of the gas spring and, therefore, move with the gas spring as the articulated support arm moves. One feature of locking release mechanism, however, is the decoupled motion of the cable assembly from the release tip of the gas spring. This allows for a more optimally constant cable path through the articulated support arm throughout the arm's entire range of motion (up/down and pivoting of the outer end) and completely decouples any changes in the cable length from the counter-balance adjustment.

Another feature of the embodiments described here is the ability of the Bowden-style cable to maintain as constant a path length as possible regardless of orientation/position of the articulated support arm. Bowden-style cables typically have a limited amount of tolerance for movement and/or bending, beyond which an unacceptable change to the cable path length can occur. Changes to the path length may cause "ghost" actuation of the gas spring (or no actuation at all).

Other embodiments concern cable management techniques for articulated support arms. Oftentimes, an articulated support arm will include one or more cables internally routed through the arm that are configured to support one or more attachments. For example, the cable(s) may be adapted for audio signals, video signals, power, etc. Conventional articulated support arms position these cable(s) either completely external to the articulated support arm, which places the cable(s) at risk of damage, or completely internal, i.e. within the body of the articulated support arm, which makes the cable(s) difficult or impossible to service. Various embodiments described herein are able to provide a unique compromise by instead designing the protective outer shell of the articulated support arm to include one or more removable pieces. Together with any non-removable pieces, the removable piece(s) preferably form a smooth surface, without protruding fasteners or covers, that is entirely or substantially free of any gaps, ridges, tight corners, or heavy textures that would make cleaning difficult.

System Overview

Figure 6:
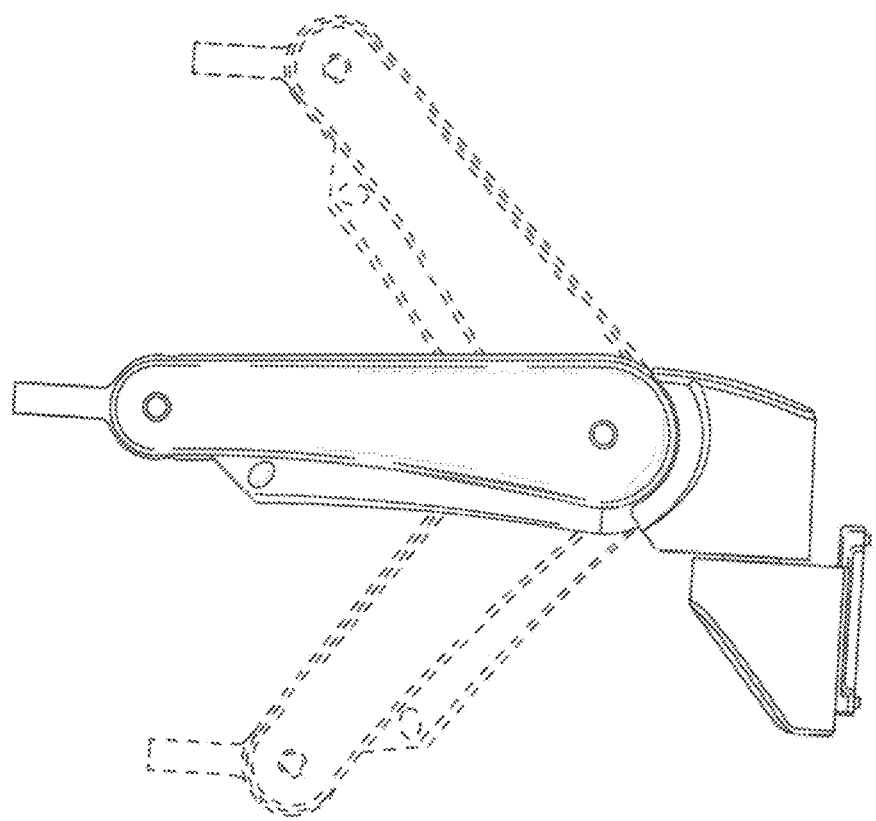
FIG. 6 illustrates how the articulated support arm is movable between various orientations.

FIG. 1 is a perspective view of an articulated support arm 100 supporting a monitor 104. The articulated support arm 100 is typically part of an assembly configured to support an object, such as a monitor 104. Other attachments can include drawers, work surfaces, computing devices, etc. The articulated support arm 100 preferably includes a gas spring that allows the vertical position to be easily changed and an outer structure 102, e.g. a protective shell, that prevents contamination and is readily cleanable. In some embodiments, the articulated support arm 100 is coupled to a handle 106 that can be used to trigger or activate a locking release mechanism. Upon being triggered, the locking release mechanism disengages the gas spring, which allows the articulated support arm 100 to be moved freely between various vertical orientations (as illustrated in FIG. 6).

Cable Management Techniques

Figure 2:
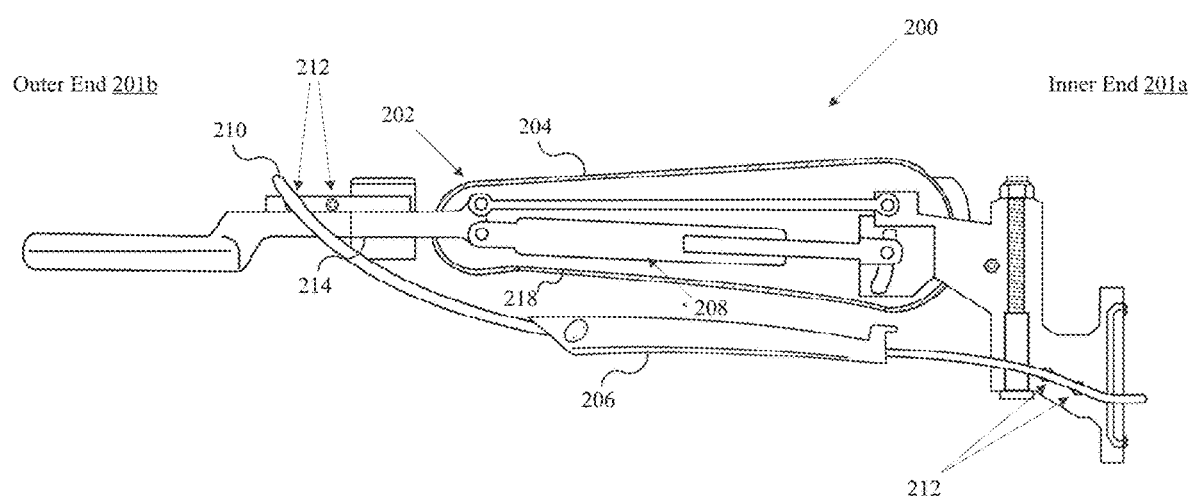
FIG. 2 is a side cutaway view of an articulated support arm in accordance with various embodiments.

FIG. 2 is a cutaway view of an articulated support arm 200 that illustrates how a gas spring 208 counter-balances the height-adjustable articulated support arm 200, as described in co-owned U.S. patent application Ser. No. 13/051,833, which is incorporated by reference herein. The articulated support arm 200 can include a protective outer structure 202 that prevents contamination and allows the articulated support arm 200 to be easily and thoroughly cleaned, e.g. within a hospital environment. The protective outer structure 202 is generally composed of an upper cover 204, a bottom cover 218, and a lower cable cover 206, some or all of which may be detachable from the articulated support arm 200. However, the outer structure 202 could be composed of any number of detachable covers that allow a user to access the internal mechanisms of the articulated support arm 200, including the gas spring 208, cables 210, and locking release mechanism.

As illustrated in FIG. 2, cables 210 are routed through the articulated support arm 200, e.g. from an inner end 201a to an outer end 201b through the lower cable cover 206. The path of the cables 210 can include a series of anchor points 212 that ensure the cables 210 remain within a predetermined path, despite the length of the cables 210 changing as the articulated support arm 200 moves between various positions. Although a single cable is shown in FIG. 2, more than one cable is typically routed through the articulated support arm 200. For example, certain embodiments may require multiple (2, 4, 8, etc.) cables of different types, e.g. audio, video, power, be routed through the articulated support arm 200. Generally, the cables 210 are selected based on which attachment(s) are affixed to the outer end 201b of the articulated support arm 200.

Figure 3:
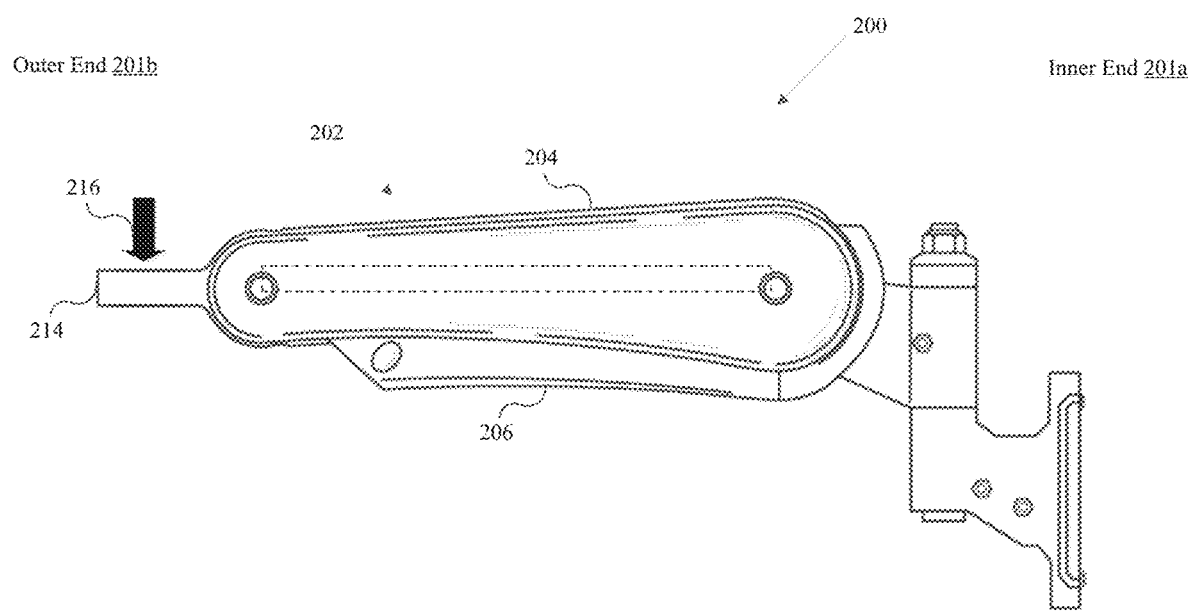
FIG. 3 is a side view of an articulated support arm in accordance with various embodiments.

When the upper cover 204 and bottom cover 218 are connected to one another, a protective outer shell 202 is formed that is substantially free of indentations, holes, etc., that would impede cleaning, as depicted in FIG. 3. Consequently, the articulated support arm 200 is easy to clean and care for. Moreover, the upper cover 204, bottom cover 218, and/or lower cable cover 206 may be easily removable, i.e. "detachably connectable," from one another, which allows a user to service the cable(s) 210 and internal components of the articulated support arm 200 without affecting cleanability of the protective outer shell 202.

The front of the mount arm 214 (shown in FIG. 3 without a handle) preferably maintains its angle throughout the articulated support arm's entire range of motion, as shown in FIG. 6. In some embodiments, the front of the mount arm 212 remains square, e.g. coplanar with respect to a horizontal plane, or vertical with respect to an applied force 216 under a full range of loads and orientations.

A bias element, such as a gas spring 208, allows the articulated support arm 200 to be moved between and locked in various vertical orientations. Although the bias element is described herein as being a gas spring 208, other bias elements could also be used, such as coil spring struts. The bias elements could also include an additional damping element that uses air, oil, an elastomeric material, or some combination thereof.

The mount arm 214 is typically connected, either directly or indirectly, to an external load that causes a force 216 to be applied through the mount arm 214 to the articulated support arm 200. The external load could be provided by, for example, a monitor or work surface. As further described below, the articulated support arm 200 can also include a locking release mechanism that allows the orientation of the articulated support arm 200 to be modified by a user.

Figure 4:
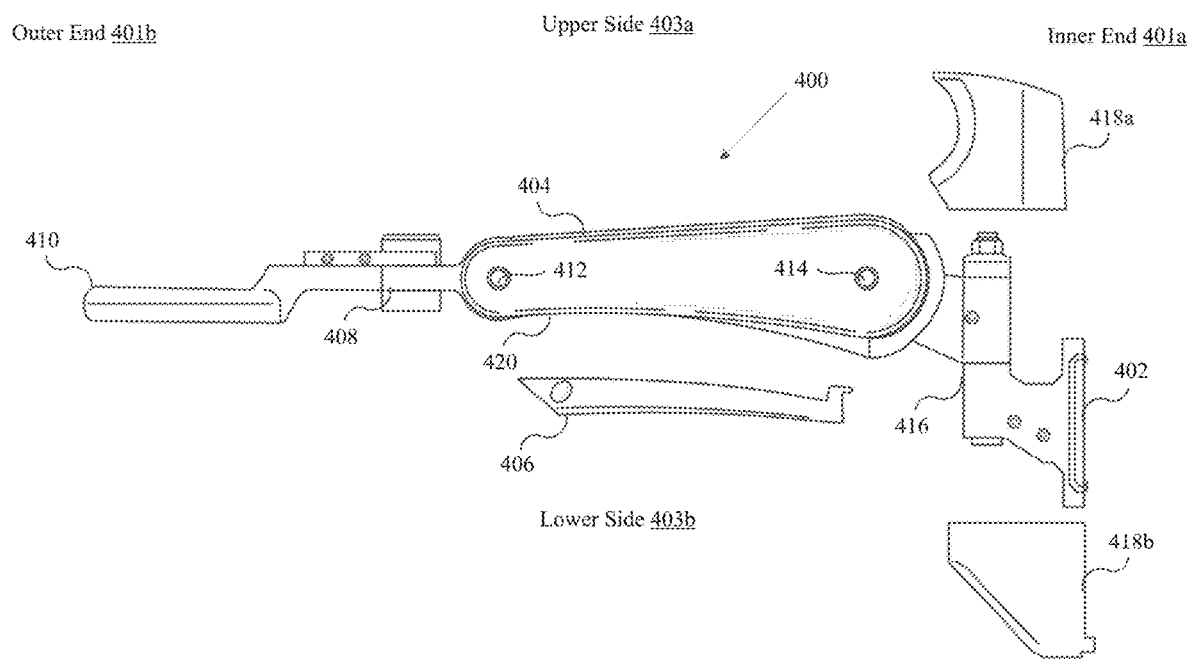
FIG. 4 is a side view of an articulated support arm that includes a mounting plate and removable outer covers as may occur in some embodiments.

FIG. 4 is an expanded side view of an articulated support arm 400 that includes a mounting plate 402 and a handle 410 (also referred to as an "adjustment mechanism") attached to the outer end 401b of the articulated support arm 400. The articulated support arm 400 can include an upper cover 404, which extends from the inner end 401a to the outer end 401b and includes opposing sides that extend downward from the upper side 403a toward the lower side 403b, and a bottom cover 420. Together, the upper cover 404 and bottom cover 420 define an interior region within the articulated support arm 400. Components of the articulated support arm 400 that would typically degrade if exposed to the operating environment, such as the gas spring and cables, can instead be safely housed within the interior region. A lower cable cover 406 allows one or more cables to be safely routed from the inner end 401a to the outer end 401b of the articulated support arm 400.

In some embodiments, each of the opposing sides of the upper cover 404 include an outer pin hole 412 and an inner pin hole 414, which allow the mount arm 408 and gas spring, as well as the corresponding strut element, to be rotatably affixed within the interior region of the articulated support arm 400. For example, opposing outer pins can be pressed through the outer pin holes 412 into corresponding pin holes in the mount arm 408. Similarly, opposing inner pins can be pressed through the inner pin holes 414 into corresponding pin holes in an extension of a pivotable base 416.

The articulated support arm 400 can be further enclosed by a lower cable cover 406 that extends across the lower side 403b of the articulated support arm 400 from the inner end 401a to the outer end 401b, one or more mount covers 418a-b, or both. For example, the lower cable cover 406 could be attached to the upper cover 404 or bottom cover 420. The mount cover(s) 418a-b are adapted to shield the pivotable base 416 and mounting plate 402. The lower cable cover 406 and/or mount cover(s) 418a-b are preferably detachable from the upper cover 404. For example, fasteners could be used to attach the lower cable cover 406 to fastener bosses defined within the upper cover 404. Other embodiments may provide other means for connecting the lower cable cover 406 to the upper cover 404 and/or bottom cover 420, such as hidden snaps, latches, detents, ridges, or other retainers that reduce manufacturing cost, improve assembly quality, reduce contamination during use, improve cleanability of the articulated support arm 400, etc.

When the lower cable cover 406 and the bottom cover are removed, components within the interior region of the articulated support arm 400 become accessible. Similarly, when the mount cover(s) 418a-b are removed, the user can access components protruding from the inner end of the body of the articulated support arm 400, as well as the mounting plate 402 (or any other suitable mounting hardware). The removable cover(s) of the articulated support arm 400 allow the user to access components that would otherwise be inaccessible due to being placed within the protective outer shell or be subjected to constant damage by being placed external to the articulated support arm 400. The techniques described herein are able to provide a unique compromise between having components completely external to the articulated support arm 400 and components that are completely internal, i.e. within the articulated support arm 400, that are impossible or nearly impossible to service.

As shown in FIG. 4, the upper cover 404 can include an opening at the inner end 401a through which the pivotable base 416 protrudes and an opening at the outer end 401b through which the mount arm 408 protrudes. The pivotable base 416, which allows the articulated support arm 400 to freely move in a horizontal manner, e.g. along a horizontal plane, may be located entirely outside of the interior region of the articulated support arm 400. In such embodiments, a structural element of the pivotable base 416 may extend into the interior region and be coupled to the gas spring and a bias element (as shown in FIG. 2).

The protective outer shell of the articulated support arm 400 preferably includes the upper cover 404, bottom cover 420, lower cable cover 406, and at least one mount cover 418a-b. Together, these covers make the outer shell clean, smooth, and well enclosed, which prevents contamination and improves cleanability. The lower cable cover 406 and the mount cover(s) 418a-b may also be collectively referred to as "cable covers" because removal of these covers allows a user to access the cables anchored to the articulated support arm 400.

In some embodiments, the upper cover 404, bottom cover 420, lower cable cover 406, and/or mount cover(s) 418a-b are composed of a die cast aluminum body, such as for strength and stiffness, and/or include a smooth powder coating that provides a durable aesthetic finish. The powder coating may include an antimicrobial additive. The top and sides of the upper cover 404 preferably form a continuous smooth surface, without protruding fasteners or covers, that is entirely or substantially free of any gaps, ridges, tight corners, or heavy textures that would make cleaning difficult.

Alternatively, the upper cover 404, bottom cover, lower cable cover 406, and/or mount cover(s) 418a-b could be composed of an injection molded plastic that provides unique contours and guide track features. For example, the mount cover(s) 418a-b may be contoured to precisely fit the inner end of the upper cover 404, thereby minimizing the exposure of the internal elements. The plastic may include polymers that are resistant to water, cleaners, disinfectants, chemicals, solutions, or any combination thereof. For example, various components can be composed of polymers, such as polypropylene (PP) or polyethylene (PE), and may further include one or more additives, such as an antimicrobial additive or an additive to prevent ultraviolet (UV) degradation.

Figure 5A:
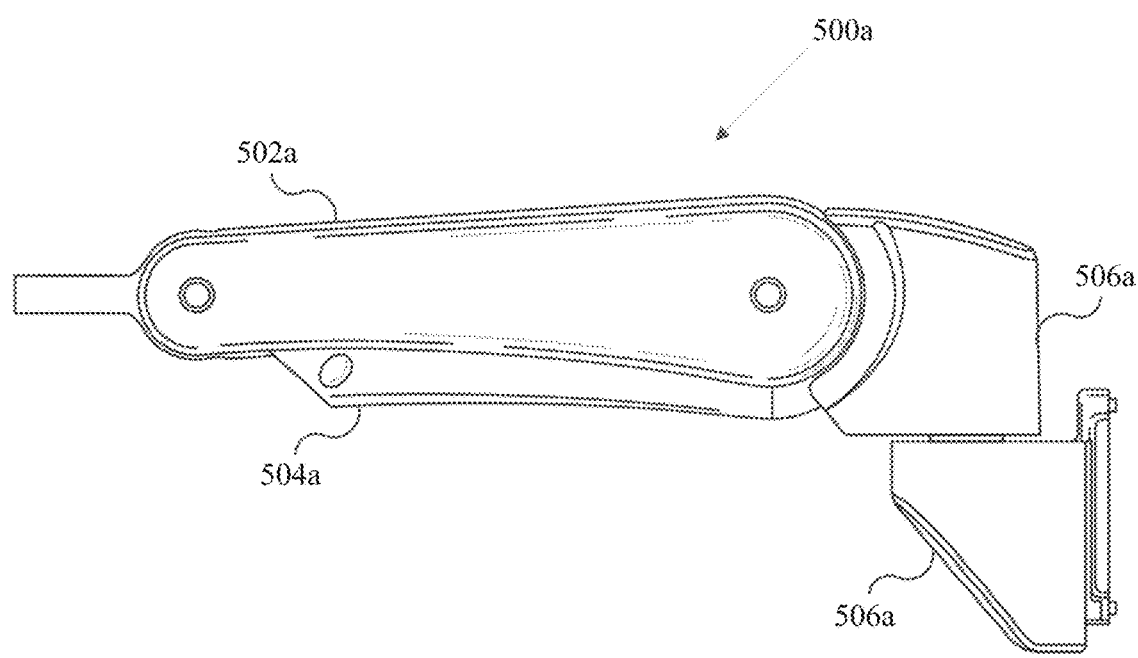
FIGS. 5A-B are side views of an articulated support arm in a "mount-plate-below" and "mount-plate-above" configuration, respectively.
Figure 5B:
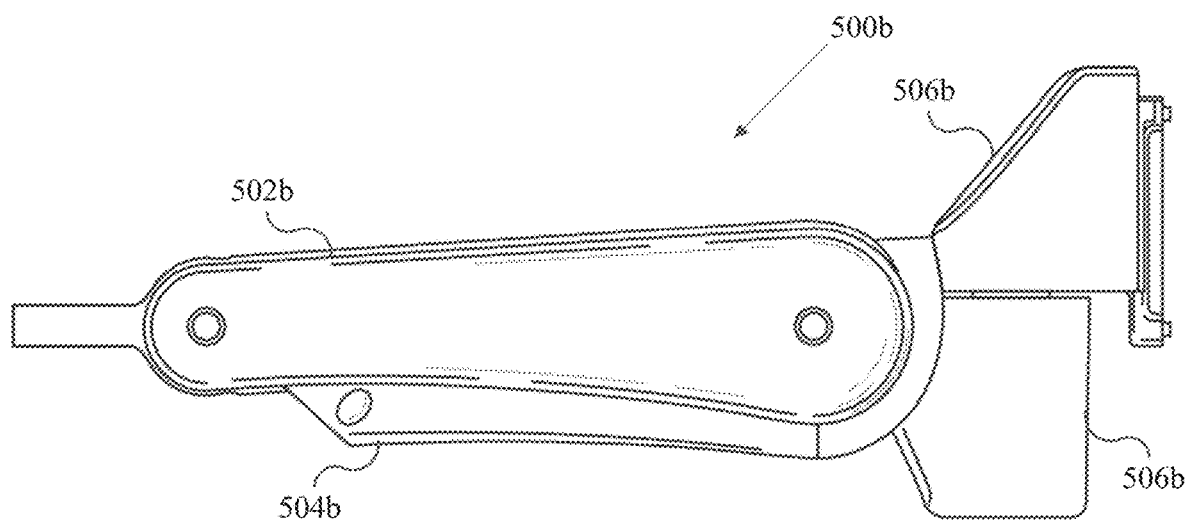

FIGS. 5A-B are side views of an articulated support arm 500a-b in "mount-plate-below" and "mount-plate-above" configurations, respectively. Although the internal mechanisms of the articulated support arm 500a-b may remain largely the same in both configurations, the geometry of the upper covers 502a-b, lower cable covers 504a-b, and mount covers 506a-b can (and often do) differ depending on the configuration. Moreover, any cables may be routed differently within the interior region of the articulated support arm 500a-b, e.g. the anchor points may be positioned in different locations. The route could also change based on the number, width, flexibility, etc., of the cables.

These configurations allow the articulated support arm 500a-b to be affixed to nearly any pre-existing mount, e.g.

mounting plates, regardless of height. For instance, a mount-plate-above configuration could be used to place the articulated support arm 500*b* (and its attachments) closer to a user situated at or below the existing mount location. Said another way, a mount-plate-above configuration may be used to position the handle and attachments nearer to the ground. Conversely, the mount-plate-below configuration could be used to elevate the articulated support arm 500*a* as well as any attachments.

FIG. 6 illustrates how the articulated support arm is movable between various vertical orientations. As further described below, the articulated support arm can be freely moved when a gas spring is disengaged, e.g. by activating a locking release mechanism, and then locked in a particular vertical orientation by re-engaging the gas spring. Generally, the articulated support arm can be locked at any vertical orientation. Because the articulated support arm is freely movable between various positions, the user can easily control the vertical orientation and horizontal position of any attachments.

However, in some embodiments, the articulated support arm is positioned in accordance with a series of predetermined vertical orientations (e.g., 0 degrees, +/−30 degrees, +/−45 degrees, etc., with respect to the horizontal plane). The articulated support arm may be adjustable upward and downward from a horizontal position by approximately 45 degrees, which yields a total range of approximately 6 inches in either direction. Other embodiments may yield more or less of a vertical range depending on the length of the articulated support arm and the pivotable range of the articulated support arm.

Figure 7:
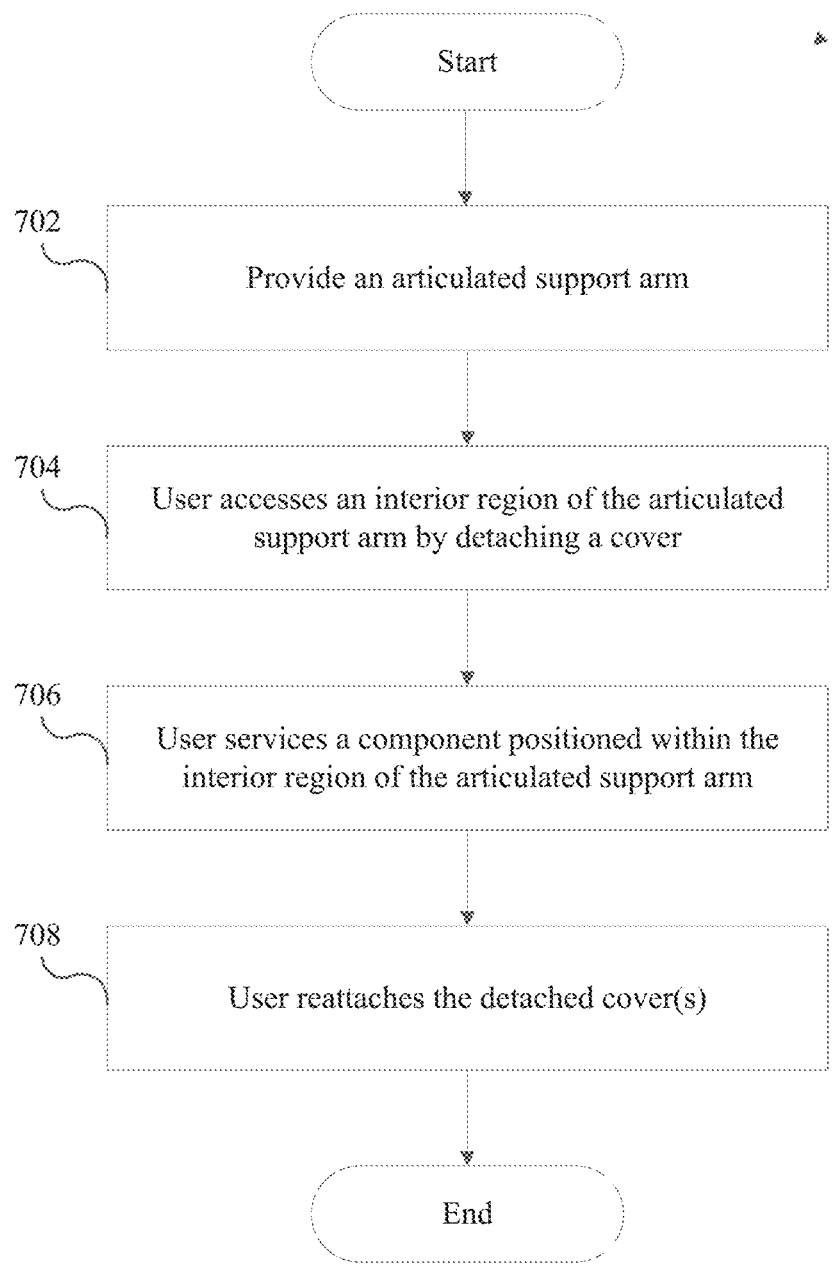
FIG. 7 depicts a process for managing and/or servicing components housed within an articulated support arm.

FIG. 7 depicts a process 700 for servicing an articulated support arm that includes one or more internal components that are housed within a protective outer shell. The internal components can be, for example, a gas spring, a gas spring release mechanism, or a cable. At step 702, an articulated support arm is provided to a user that includes a protective outer shell and through which at least one cable is routed. The cable could be, for example, a coaxial cable, fiber optic cable, high-definition multimedia interface (HDMI), power cable, Ethernet cable, etc. The protective outer shell is composed of an upper cover and bottom cover (that together form the body of the articulated support arm), a lower cable cover, one or more mount covers, or some combination thereof, at least one of which is detachable from the articulated support arm.

At step 704, the user accesses the interior region of the articulated support arm by removing one of the covers (e.g., the upper cover or the bottom cover) that form the protective outer shell. Removal of the cover(s) permits the user to easily service an internal component that would typically be inaccessible. In some embodiments some subset of the covers are removable by the user, while in other embodiments each of the covers is removable by the user. For example, the user may be able to remove the upper cover to access the gas spring, the bottom cover to access a power cable, and the mount cover(s) to access a mounting plate that fixedly attaches the articulated support arm to a mounting surface, e.g. wall. Similarly, the user can access one or more cables routed proximate to the articulated support arm by removing the lower cable cover.

At step 706, the user is able to service the internal component. For example, the user may elect to route a new cable through the lower cable cover attached to the articulated support arm. As another example, the user could choose to repair or replace the gas spring within the articulated support arm. Such modifications cannot be easily performed on conventional support arm assemblies. Instead, the user would have to replace the articulated support arm as a whole or have the articulated support arm deconstructed and repaired by an experienced professional. At step 708, the user completes the servicing by reattaching the detached cover(s).

Unless contrary to physical possibility, it is envisioned that the steps described above may be performed in various sequences and combinations. For instance, a user may elect to periodically detach pieces of the outer shell of the articulated support arm to service various internal components, while also continuing to use the articulated support arm regularly, e.g. by freely moving the articulated support arm between various positions and orientations.

Locking Release Mechanism

Figure 8:
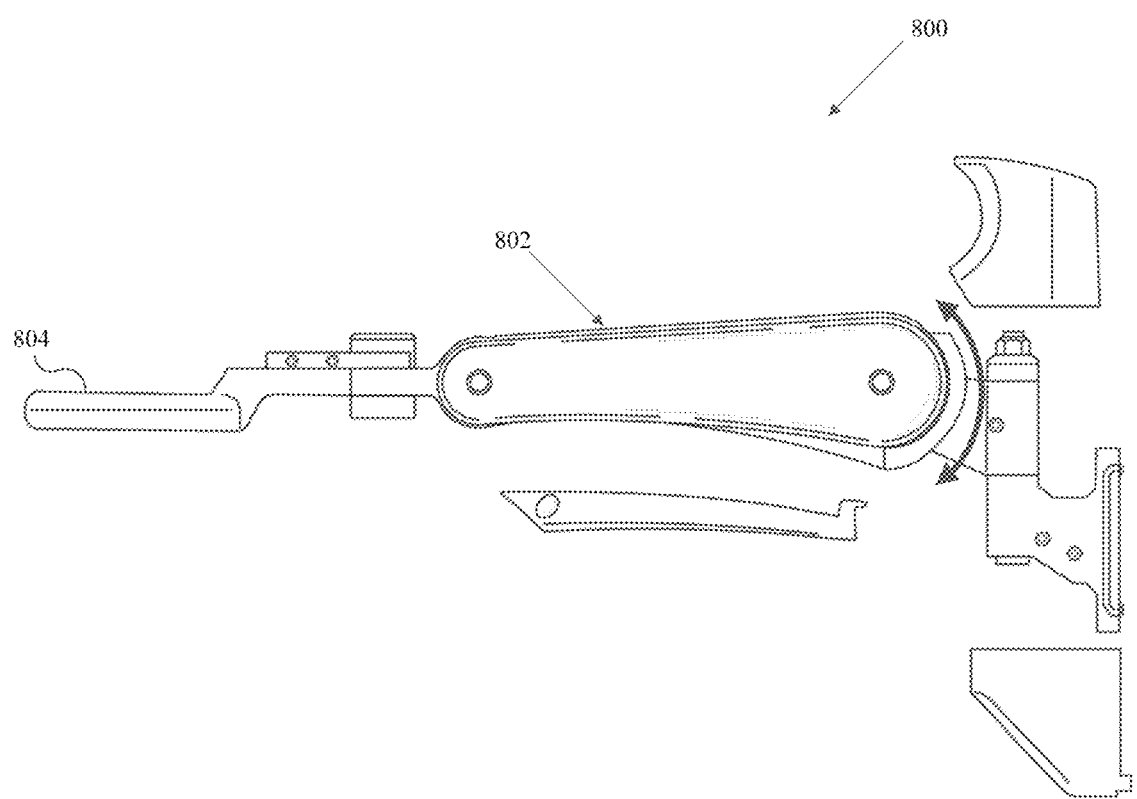
FIG. 8 is a side view of an articulated support arm that includes a locking release mechanism for a gas spring housed within the body of the articulated support arm.

FIG. 8 is a side view of an articulated support arm 800 that includes a locking release mechanism for a gas spring housed within the body 802 and handle 804 of the articulated support arm 800. The locking release mechanism includes a handle release mechanism positioned within the handle 804 and a gas spring release mechanism positioned within the body 802 of the articulated support arm 800. A Bowden-style control cable assembly extends from the handle release mechanism to the gas spring release mechanism.

Figure 9:
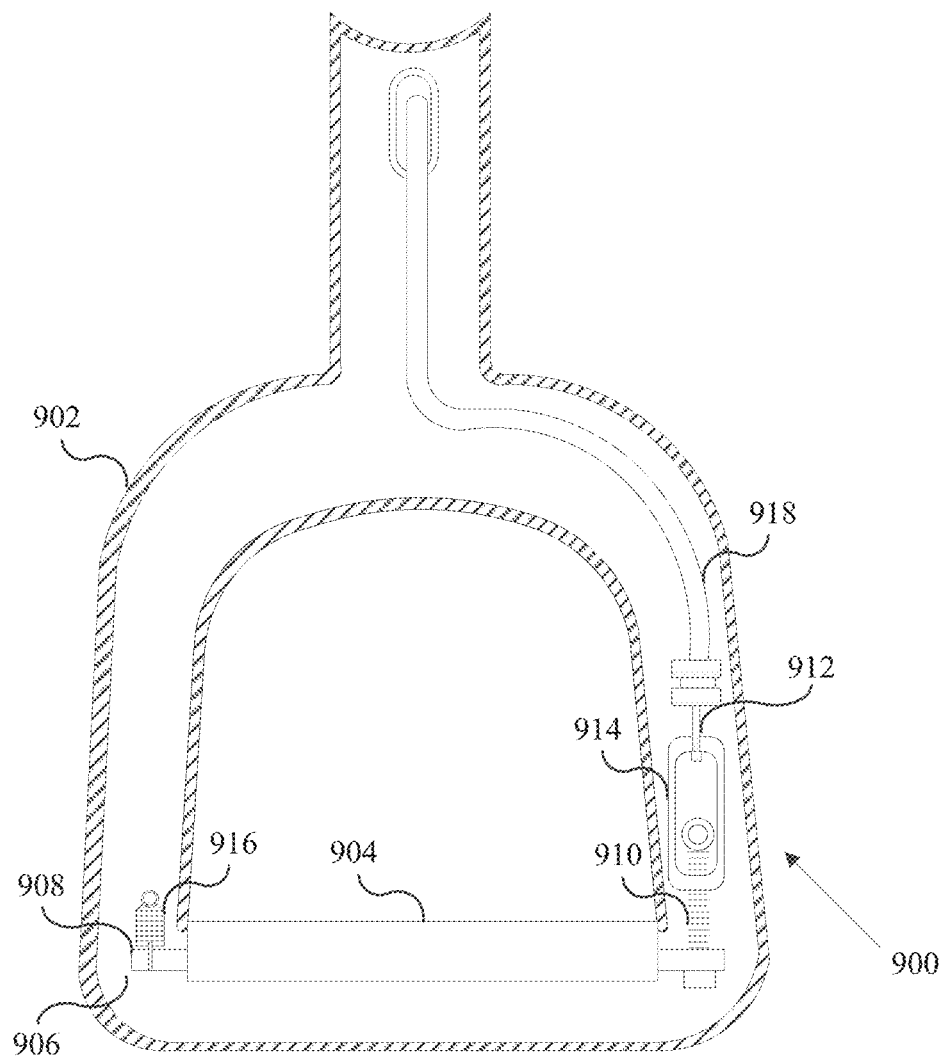
FIG. 9 is a cutaway view of the handle within which the handle release mechanism is located.
Figure 12:
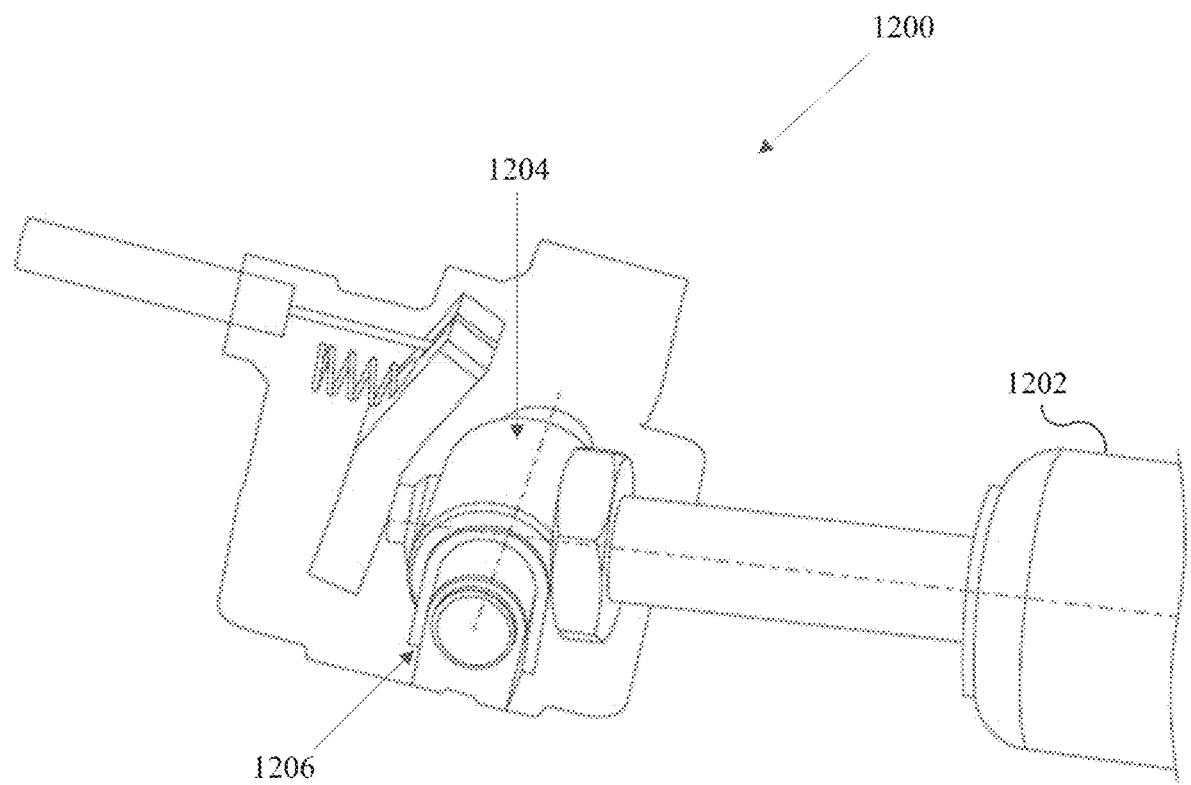
FIG. 12 is a perspective view of the gas spring release mechanism, which includes a pivoting trunnion mount and a fixed actuation lever pivot.
Figure 13:
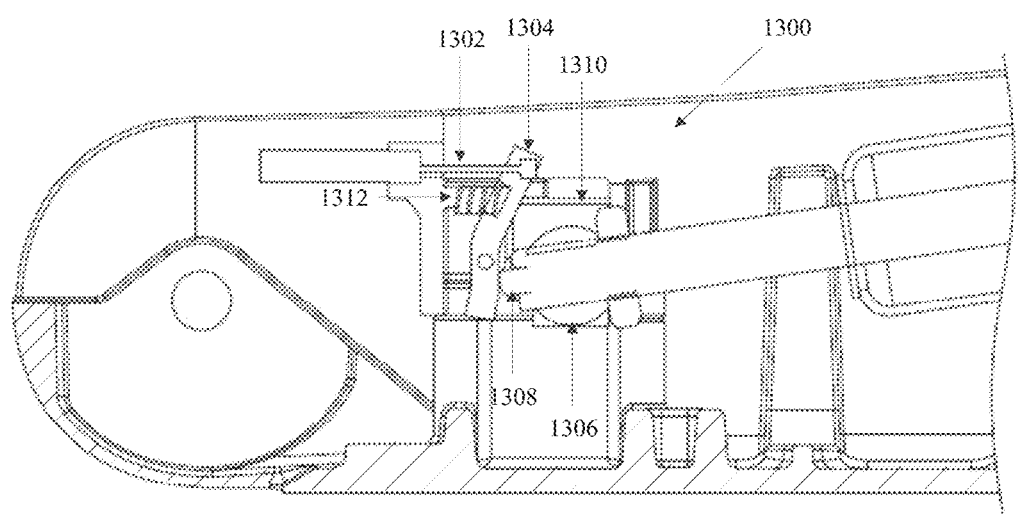
FIG. 13 is a side cutaway view of the gas spring release mechanism positioned within the body of an articulated support arm.

More specifically, the handle 804 includes a release mechanism (as shown in FIG. 9) that allows the user to apply pressure and engage the handle release mechanism. Upon being engaged, the handle release mechanism pulls a release cable, which causes the gas spring release mechanism (as shown in FIGS. 12-13) to depress the release tip of the gas spring. The gas spring remains locked, i.e. the piston will not move freely, unless the release tip of the gas spring is depressed.

When the release tip is depressed, the user is able to freely modify the vertical orientation of the articulated support arm 800, i.e. along the path illustrated by FIGS. 6 and 8. However, when the release mechanism is disengaged, pressure is once again asserted on the gas spring by the release tip and the articulated support arm 800 is locked in place.

FIG. 9 is a top cutaway view of the handle release mechanism 900 within the handle 902 of the articulated support arm. The handle release mechanism 900 is engaged by a grip actuator 904, e.g. a squeeze plate, that pivots about a grip actuator axle 906 that is translationally fixed to the body of the handle 902. A grip actuator rod 908 is captured within the grip actuator 904 such that the grip actuator rod 908 moves with the grip actuator 904, but is also free to rotate about the grip actuator rod's axis to maintain a preferred alignment while moving. That is, the grip actuator rod 908 can rotate freely to adjust the tension applied to a release cable 912 by a tensioner block 914 when the grip actuator 904 is squeezed.

The preferred alignment is aligned with a tensioner screw 910, which is also in-line with the axis of the release cable 912 that connects the handle release mechanism 900 to the gas spring release mechanism within the body of the articulated support arm. The path of the release cable 912 is selected to minimize the change in path length over the full range of motion of the articulated support arm. More specifically, the path length of the release cable 912 is typically designed to remain substantially consistent as the articulated support arm pivots up and down and rotates left and right. In some embodiments, the release cable 912 is a Bowden-style fixed length cable assembly that includes a protective jacket or sheath 918.

When pressure is applied to the grip actuator 904, the tensioner screw 910 is pulled by the grip actuator rod 908.

The tensioner screw 910 has a threaded connection to a tensioner block 914, which is coupled to the end of the release cable 912. The tensioner block 914, which serves as a structural connector between the tensioner screw 910 and the release cable 912, can bias against resistance at the opposite end of the grip actuator rod 908, e.g. supplied by a spring 916. The other end of the release cable 912 is connected to the gas spring release mechanism in the body of the articulated support arm.

A spring 916 could also be used to balance the tension applied by the release cable 912 through the tensioner screw 910 to the grip actuator rod 908. Together, the spring 916 and the release cable 912 bias the grip actuator rod 908 so that a user is able to comfortably apply pressure to the grip actuator 904 without experiencing racking or an uneven resistive force. The grip actuator axle 906 positioned substantially parallel to the grip actuator rod 908 can also support the grip actuator 904 in a rigid manner and prevent the grip actuator from racking as pressure is applied by the user.

Figure 10A:
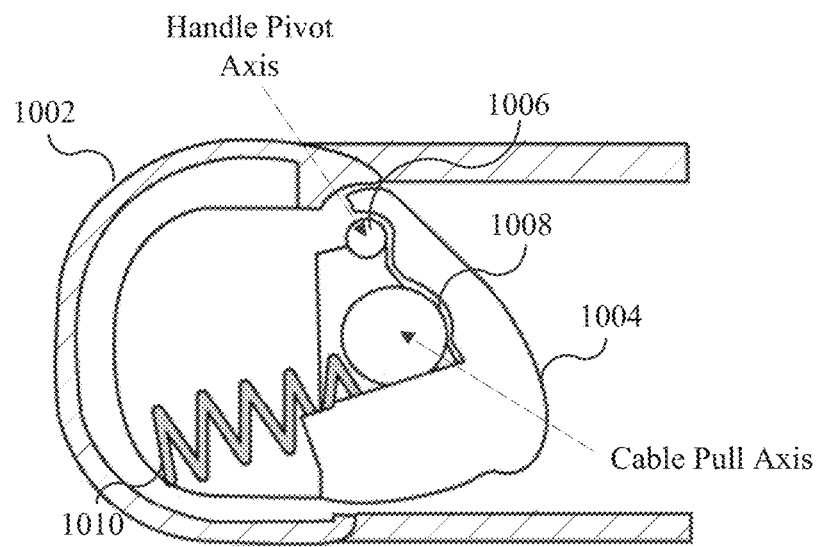
FIGS. 10A-B are side cutaway views that illustrate how the handle release mechanism is triggered when pressure is applied to a grip actuator.
Figure 10B:
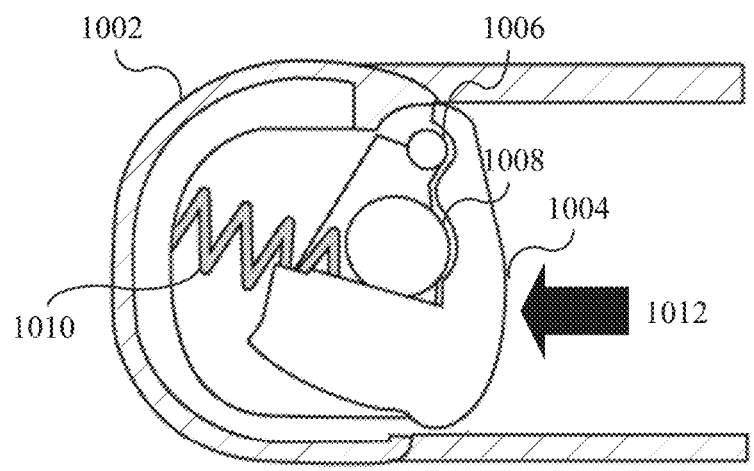

FIGS. 10A-B are side cutaway views of the handle 1002 that illustrate how the handle release mechanism is triggered when pressure is applied to the grip actuator 1004. More specifically, FIGS. 10A-B depict the grip actuator 1004, grip actuator axle 1006, grip actuator rod 1008, and spring 1010 in a locked and unlocked position, respectively.

As shown in FIG. 10A, the tension supplied by the spring 1010 and release cable (not pictured) cause the grip actuator 1004 to naturally extend away from the body of the handle 1002. When no pressure is applied to the grip actuator 1004, the gas spring continues to be engaged and the articulated support arm remains in a static, i.e. locked, position. In some embodiments, the distance between the axes of the grip actuator axle 1006 and the grip actuator rod 1008 is designed for a certain mechanical ratio in order to improve gas spring actuation. Said another way, the locations of the grip actuator axle 1006 and grip actuator rod 1008 may be selected to minimize the amount of pressure 1012 needed to be applied by the user to trigger the hand release mechanism.

When pressure 1012 is applied to the grip actuator 1004 by the user, as shown in FIG. 10B, the grip actuator 1004 pivots about the grip actuator axle 1006, which causes the grip actuator rod 1008 to pull the tensioner screw, tensioner block, and release cable. Pulling of the release cable disengages the gas spring and allows the articulated support arm to be freely moved. Once the pressure 1012 is removed from the grip actuator 1004, the grip actuator 1004 returns to the locked position depicted by FIG. 10A. The return action of the grip actuator 1004 is caused by a combination of the internal pressure of the gas spring (relayed by the release cable) and the spring 1010 placed within the handle 1002. Consequently, the gas spring remains locked and the articulated support is immovable unless the grip actuator 1004 is engaged by a user. The locking release mechanism, i.e. the handle release mechanism and gas spring release mechanism, is able to translate the pressure caused by the user's hand squeeze into a force that causes the tip of the gas spring to be depressed and pressure to be relieved.

Figure 11:
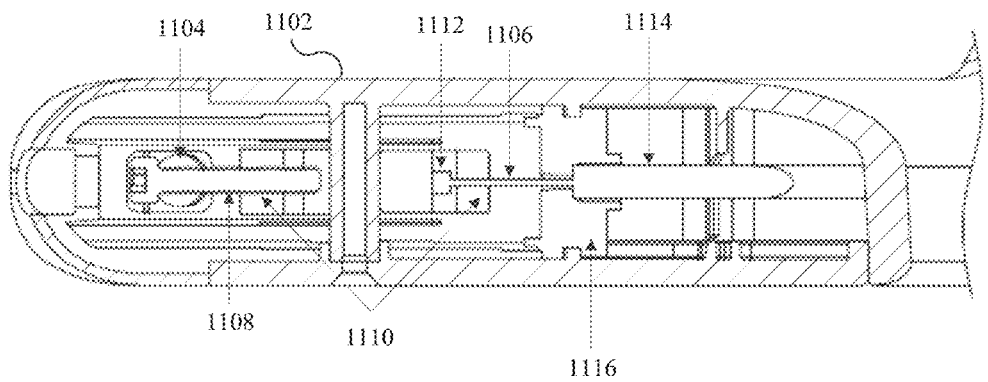
FIG. 11 is a side cutaway view of the handle release mechanism depicting how movement of the actuator rod causes tension to be applied to a cable coupled to the gas spring release mechanism.

FIG. 11 is a side cutaway view of the handle 1102 that illustrates how movement of the grip actuator rod 1104 causes tension to be applied to the release cable 1106 coupled to the gas spring release mechanism. The side view presented here is opposite the side views presented in FIGS. 10A-B. When the grip actuator rod 1104 is displaced by movement of the grip actuator, the tensioner screw 1108 is pulled, which causes the tensioner block 1110 to pull the end of the release cable 1106.

In some embodiments, the release cable 1106 includes a cable end fitting 1112 that securely couples the release cable 1106 to the tensioner block 1110. The release cable 1106 may also be placed within a cable conduit 1114 that protects the release cable 1106 as it extends from tensioner block 1110 of the handle release mechanism to the gas spring release mechanism. The handle 1102 may also include other structural elements that help maintain the position of the components described herein. For example, a cable housing stop block 1116 may receive one end of the cable conduit 1114 and ensure the release cable 1106 terminates within the handle at a specific location.

FIG. 12 is a perspective view of the gas spring release mechanism 1200. The gas spring 1202 is pivotably mounted to a trunnion 1204, which is captured by a trunnion mount 1206 that is fixedly attached to the articulated support arm, and bushings. The trunnion 1204 allows the gas spring 1202 to pivot about the trunnion axis relative to the body of the articulated support arm (as well as the other components of the gas spring release mechanism 1200). The pivoting motion described herein allows the vertical orientation of the articulated support arm to be adjusted and also accommodates changes in the angle of the gas spring due to counter balance adjustments.

FIG. 13 is a side cutaway view gas spring release mechanism 1300, including the release cable 1302, pivot lever 1304, trunnion 1306, and gas spring release pin 1308. One feature of the gas spring release mechanism 1300 is the decoupled motion of the release cable 1302 from the gas spring release pin 1308. This allows for a more optimal, e.g. substantially constant, cable path through the articulated support arm throughout the arm's entire range of motion and also completely decouples any changes in length from the counter-balance adjustment.

The release cable 1302 is attached to one end of the pivot lever 1304. The pivot lever 1304, as well as the trunnion 1306, may be supported by a trunnion mount 1310 that is anchored within the body of the articulated support arm. When tension is applied to the release cable 1302, the pivot lever 1304 rotates about a fixed point (and, more specifically, a pivot axis that extends through the gas release mechanism 1300. The form of the pivot lever 1304 generally accommodates the pivoting motion. Moreover, in some embodiments, the pivot lever 1304 balances the tension provided by the gas spring release pin 1308 and a return spring 1312.

Figure 14A:
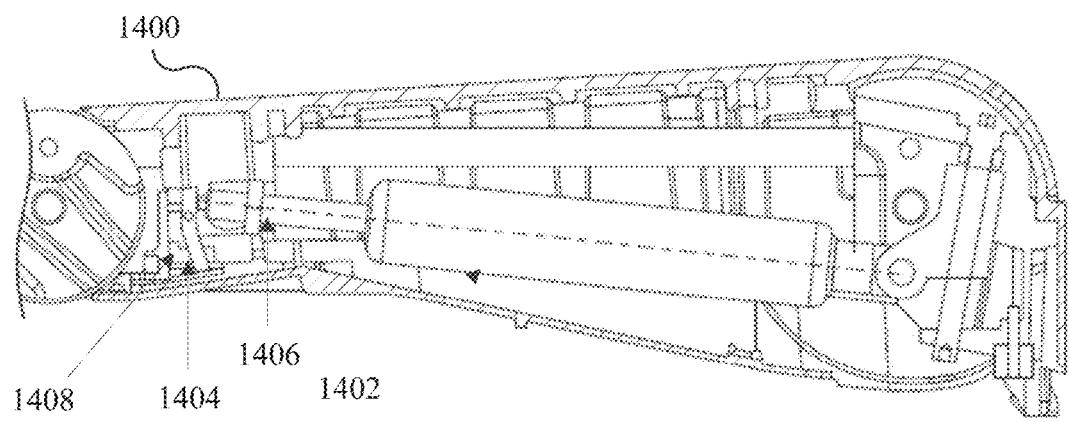
FIGS. 14A-C are side cutaway views demonstrating how activation of the gas spring release mechanism causes decoupled motion of the articulated support arm.
Figure 14B:
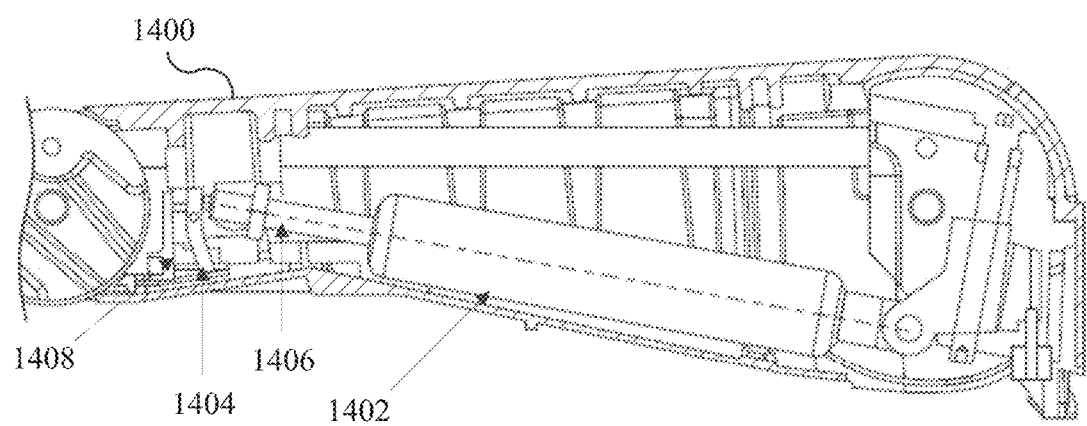
Figure 14C:
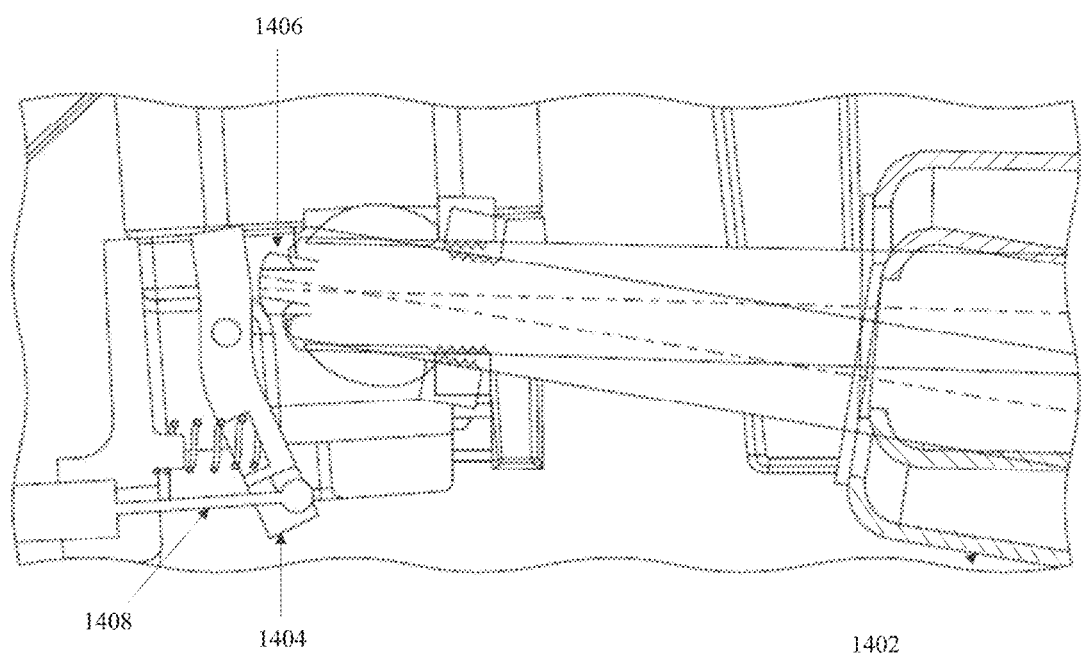

FIGS. 14A-C are side views of the articulated support arm 1400 that demonstrate the decoupled motion of the gas spring 1402 from the body of the articulated support arm 1400. More specifically, FIG. 14C illustrates the various gas spring positions that can be accommodated when the counter-balance force is low (as shown in FIG. 14A where the counter balance adjuster block is high) and when the counter-balance force is high (as shown in FIG. 14B where the counter balance adjuster block is low).

The decoupled motion of the gas spring 1402 from the pivot lever 1404 accommodates relative motion between the two components. Generally, counter-balance adjustment requires approximately five degrees of motion, while movement of the articulated support arm up/down requires approximately four degrees of motion. The combination of counter-balancing and arm motion requires approximately seven degrees of motion in total. A release pin 1406 affixed to the end of the gas spring 1402 is configured to move along with the gas spring 1402.

The motion of the components of the gas spring release mechanism, such as the pivot lever 1404, would typically present functional and packaging challenges e.g. size constraints of the arm body. However, the techniques described herein solve these challenges by rotatably affixing the release pin 1406 of the gas spring 1402 to the pivot lever 1404 of the gas spring release mechanism.

For example, maintaining as near a constant path length as possible for the Bowden-style release cable 1408 is critical because the release cable 1408 has a limited tolerance for movement and bending, beyond which an unacceptable change to the release cable path occurs. The change can cause "ghost" actuation of the gas spring release mechanism or no actuation at all. The techniques described here prevent movement of the articulated support arm from changing the path length of the release cable 1408, which could cause the release cable 1408 to pull the pivot lever 1404 and undesirably "ghost" actuate the gas spring release mechanism.

Figure 15:
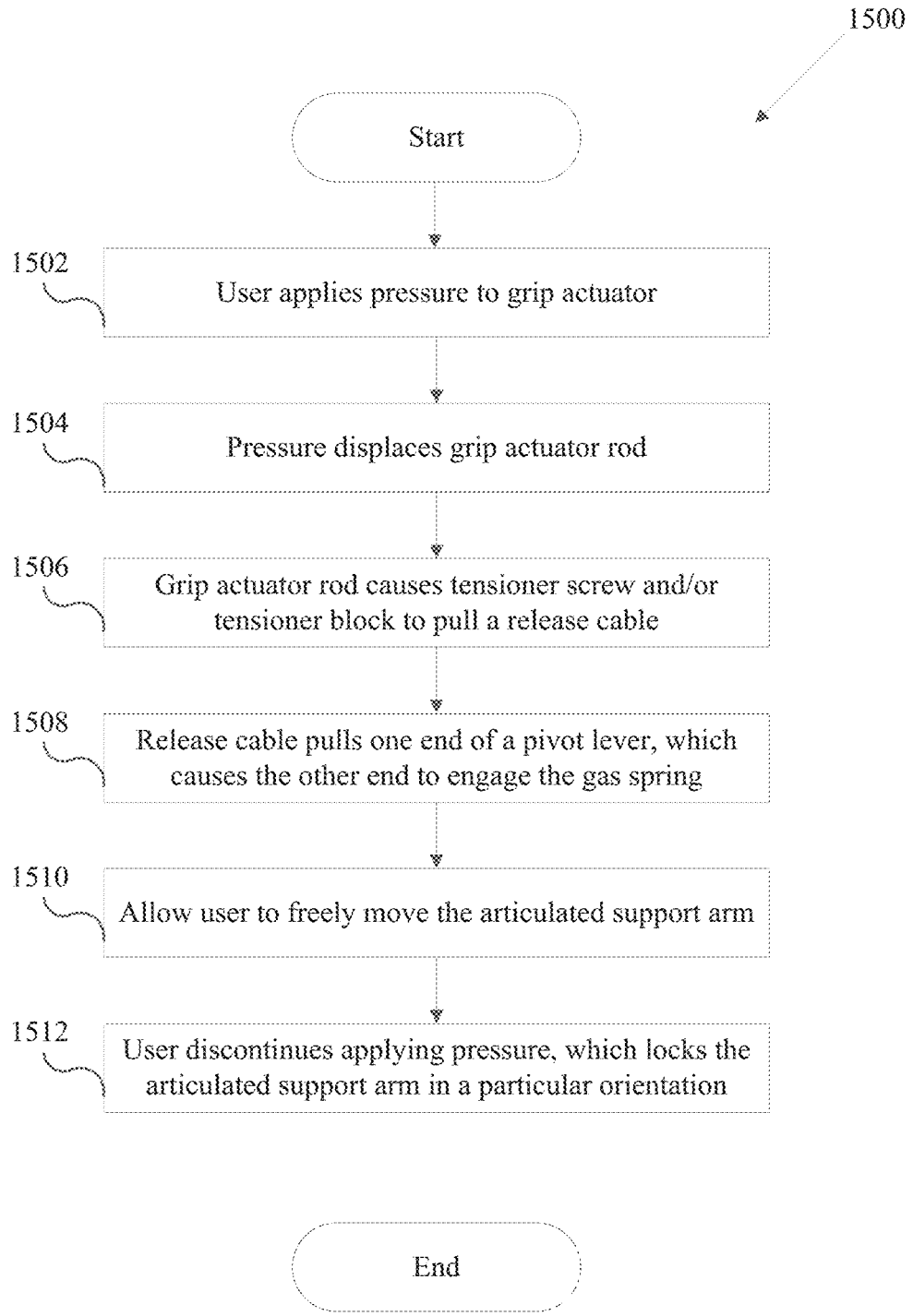
FIG. 15 depicts a process for modifying the vertical orientation of an articulated support arm that includes a locking release mechanism.

FIG. 15 depicts a process 1500 for disengaging a gas spring of an articulated support arm, which allows a user to freely move the articulated support arm between various vertical orientations. At step 1502, the user applies pressure to a grip actuator positioned within the handle of the articulated support arm. The grip actuator could be, for example, a squeeze plate that is biased on each end to provide an evenly distributed resistive force.

At step 1504, the pressure displaces a grip actuator rod, which causes a tensioner screw and/or tensioner block to pull one end of a release cable, as shown at step 1506. The release cable, which may be part of a Bowden-style fixed length cable assembly that includes a protective jacket, couples the tensioner block to a pivot lever within the body of the articulated support arm. At step 1508, the release cable pulls one end of the pivot lever, which causes the other end to apply pressure to the release tip of the gas spring. In some embodiments, the release tip of the gas spring is pivotably mounted to a trunnion that allows the gas spring to rotate as the articulated support arm moves without mistakenly engaging the gas spring.

Once the gas spring has been engaged, the articulated support arm can be freely moved by the user, as shown at step 1510. At step 1512, the user discontinues applying pressure to the grip actuator, e.g. by releasing the squeeze plate, which disengages the gas spring and locks the articulated support arm in a particular orientation.

The language used in the Detailed Description has been principally selected for readability and instructional purposes, and it may not have been selected to delineate or circumscribe the inventive subject matter. It is therefore intended that the scope of the technology be limited not by the Detailed Description, but rather by any claims that issue on an application based hereon. Accordingly, the disclosure of various embodiments is intended to be illustrative, but not limiting, of the scope of the embodiments, which is set forth in the following claims.

The invention claimed is:

1. A method of operating an articulated support arm, the method comprising:
   in response to a pressure being applied to an actuator positioned in a handle of the articulated support arm,
      displacing a rod that is biased at a first end by a spring and biased at a second end by a tension mechanism secured to a first end of a cable in a direction that is coplanar with the first end of the cable, thereby causing tension to be applied to the cable that is connected between the tension mechanism and a lever positioned in a body of the articulated support arm; and
      causing the lever to pivotably engage a release pin of a gas spring,
         wherein engagement of the release pin allows the articulated support arm to freely move along a vertical plane.

2. The method of claim 1, wherein said displacing is performed by the actuator, and wherein said causing is performed by the cable.

3. The method of claim 1, further comprising:
   in response to the pressure being removed from the actuator,
      causing the rod to automatically return to its original position.

4. The method of claim 3,
   wherein when the rod is in its original position, tension is not applied to the first end of the cable, and
   wherein the lack of tension applied to the first end of the cable causes the lever to disengage the release pin of the gas spring, thereby causing the articulated support arm to be locked in a particular vertical orientation.

5. The method of claim 1, wherein when tension is applied to the first end of the cable by the tension mechanism, a second end of the cable pulls a first end of the lever, thereby causing a second end of the lever to pivotably engage the release pin of the gas spring.

6. The method of claim 1, wherein movement of the cable is decoupled from movement of the release pin to prevent unintended actuation of the gas spring.

7. A method of operating an articulated support arm that includes (i) a handle with an actuator positioned therein and (ii) a body with a bias element positioned therein, the method comprising:
   applying pressure to the actuator in a direction that is coplanar with an axis of a first end of a cable that extends from the handle to the body, so as to apply tension to the first end of the cable,
      wherein when the tension is applied to the first end of the cable, a second end of the cable pulls a first end of a lever located in the body, thereby causing a second end of the lever to pivotably engage the bias element; and
   moving the articulated support arm along a vertical plane while pressure is continuously applied to the actuator.

8. The method of claim 7, further comprising:
   removing the pressure from the actuator in response to determining that the articulated support arm is positioned in a desired vertical orientation, so as to remove the tension from the first end of the cable.

9. The method of claim 8, wherein when the tension is removed from the first end of the cable, the second end of the cable ceases pulling the first end of the lever located in the body, thereby causing the second end of the lever to disengage the bias element.

10. The method of claim 9, wherein the articulated support arm is locked in the desired vertical orientation when the second end of the lever disengages the bias element.

11. A locking release system comprising:
   a first release mechanism that includes:
      an actuator that is connected to a first end of a cable, wherein when pressure is applied to the actuator in a direction that is coplanar with an axis of the first end of the cable, tension is applied to the first end of the cable; and
   a second release mechanism that includes:

a lever that has (i) a first end that is connected to a second end of the cable and (ii) a second end that is able to pivotably engage a bias element, wherein when the tension is applied to the first end of the cable, the second end of the cable pulls the first end of the lever, thereby causing the second end of the lever to pivotably engage the bias element.

12. The locking release system of claim 11, wherein the first release mechanism further includes:

a rod that is captured within the actuator such that the rod moves with the actuator when the pressure is applied, and a tension mechanism that is connected between the rod and the first end of the cable.

13. The locking release system of claim 12, wherein the tension mechanism includes:

a tensioner block that is connected to the first end of the cable, and a tensioner screw that is connected between the rod and the tensioner block.

14. The locking release system of claim 11, wherein the second release mechanism further includes:

a trunnion to which the bias element is pivotably mounted, and a mount that secures the trunnion to an interior surface of a structure in which the bias element is installed.

15. The locking release system of claim 11, wherein the first release mechanism is positioned in a handle of an articulated support arm, and wherein the second release mechanism is positioned in a body of the articulated support arm.

16. The locking release system of claim 15, wherein the actuator is a squeeze plate accessible along a surface of the handle of the articulated support arm.

17. The locking release system of claim 15, wherein engagement of the bias element allows the articulated support arm to be freely moved along a vertical plane.

18. The locking release system of claim 11, wherein the bias element is a gas spring.

19. The locking release system of claim 11, wherein the cable is part of a fixed-length cable assembly that includes an outer sheath.

* * * * *